United States Patent [19]

Lau et al.

[11] Patent Number: 5,250,667

[45] Date of Patent: Oct. 5, 1993

[54] 1-[(HYDROXYPHENOXY)PHENYLENE]-TRIAZENES, POLYMERS CROSSLINKED THEREWITH, AND METHODS THEREFOR

[75] Inventors: Aldrich N. K. Lau, Palo Alto; Lanchi P. Vo, San Jose, both of Calif.

[73] Assignee: Raychem Corporation, Menlo Park, Calif.

[21] Appl. No.: 943,093

[22] Filed: Sep. 9, 1992

[51] Int. Cl.$^5$ .................. C07C 245/24; C08L 71/12
[52] U.S. Cl. .................. 534/554; 534/550; 525/390; 525/905
[58] Field of Search ............... 534/550, 554; 525/390, 525/905

[56] References Cited

FOREIGN PATENT DOCUMENTS

| | | |
|---|---|---|
| WO91/09070 | 6/1991 | PCT Int'l Appl. |
| WO91/09071 | 6/1991 | PCT Int'l Appl. |
| WO91/09081 | 6/1991 | PCT Int'l Appl. |
| WO91/09087 | 6/1991 | PCT Int'l Appl. |
| WO91/16369 | 10/1991 | PCT Int'l Appl. |
| WO91/16370 | 10/1991 | PCT Int'l Appl. |

*Primary Examiner*—James J. Seidleck
*Assistant Examiner*—Thomas Hamilton, III
*Attorney, Agent, or Firm*—Herbert G. Burkard; Yuan Chao

[57] ABSTRACT

Compounds of the structure

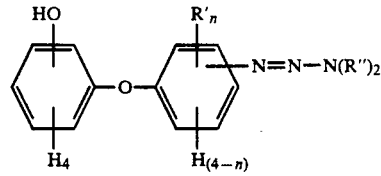

where $-R'$ is $-F$, $-CF_3$, $-CN$, or $-Cl$; each $-R''$, which may be the same or different, is independently selected from the group consisting of $C_1-C_6$ alkyl or hydroxyalkyl moieties and aryl moieties; and n is 0 or 1. Such compounds are useful as derivatizing and crosslinking agents for polymers, especially fluorinated poly(arylene ethers).

7 Claims, No Drawings

1-[(HYDROXYPHENOXY)PHENYLENE]TRIAZENES, POLYMERS CROSSLINKED THEREWITH, AND METHODS THEREFOR

TECHNICAL FIELD OF THE INVENTION

This invention relates to 1-[(hydroxyphenoxy)-phenylene]triazene compounds, methods for crosslinking polymers therewith, and crosslinkable polymer compositions made therefrom.

BACKGROUND OF THE INVENTION

It has been proposed to use fluorinated poly(arylene ethers) for electronic applications, such as insulators or passivation layers in multilayer integrated circuit devices or multichip modules. Mercer, WO 91/09070 (1991); Mercer et al., WO 91/16369 (1991). Their advantages include chemical inertness, low dielectric constant, insensitivity to ambient humidity, and ease of coating over a substrate.

Fluorinated poly(arylene ethers) may be crosslinked to improve solvent resistance and/or help preserve mechanical properties at elevated temperatures. Bistriazene crosslinking agents whose triazene groups decompose upon heating and form reactive crosslinking centers have been used. Lau et al., WO 91/09087 (1991); Mercer et al., WO 91/09081 (1991) and WO 91/09071 (1991). It has also been proposed to use oligomers which are crosslinkable via reactive terminal groups. Mercer et al., WO 91/16370 (1991). The crosslinking of fluorinated poly(arylene ethers) with triazenic oxadiazole compounds is disclosed in Mercer et al., application Ser. No. 07/943370, filed even date herewith.

We have discovered new compounds which are effective crosslinking agents for fluorinated poly(arylene ethers).

SUMMARY OF THE INVENTION

This invention provides a compound of the structure

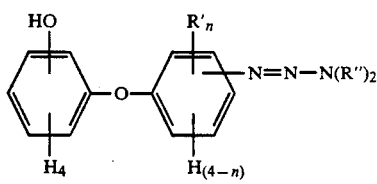

where —R' is —F, —CF$_3$, —CN, or —Cl; each —R", which may be the same or different, is independently selected from the group consisting of C$_1$-C$_6$ alkyl or hydroxyalkyl moieties and aryl moieties; and n is 0 or 1.

This invention also provides a method of crosslinking a fluorinated poly(arylene ether), comprising the steps of:

(a) providing a fluorinated poly(arylene ether) having a repeat unit of the structure

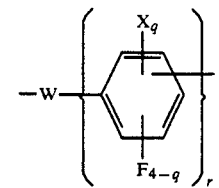

wherein
—W— is

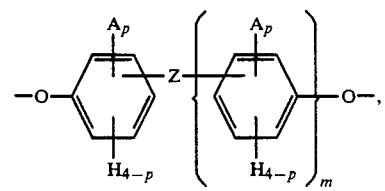

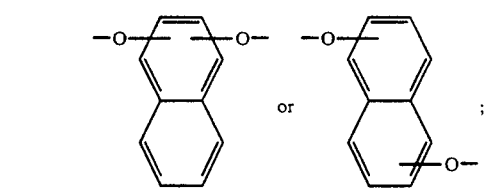

wherein each —A is independently —F, —Cl, —Br, —CF$_3$, —CH$_3$, —CH$_2$CH=CH$_2$, or —C$_6$H$_5$; p is 0, 1, or 2; —Z— is a direct bond, —C(CH$_3$)$_2$—, —C(CF$_3$)$_2$—, —O—, —S—, —SO$_2$—, —CO—, —P(C$_6$H$_5$)—, —C(CH$_3$)(C$_6$H$_5$)—, —C(C$_6$H$_5$)$_2$—, —(CF$_2$)$_{1-6}$—, or

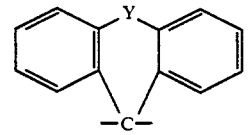

wherein —Y— is —O— or a direct bond; and m is 0, 1, or 2;
each —X is independently —H, —Cl, —Br, —CF$_3$, —CH$_3$, —CH$_2$CH=CH$_2$, or —C$_6$H$_5$;
q is 0, 1, or 2; and
r is 1 or 2;

(b) reacting the fluorinated poly(arylene ether) with a compound of the structure

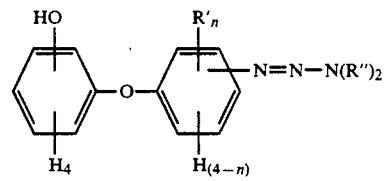

where —R' is —F, —CF$_3$, —CN, or —Cl; each —R", which may be the same or different, is independently selected from the group consisting of C$_1$-C$_6$ alkyl or hydroxyalkyl moieties and aryl moieties; and n is 0 or 1, to form a triazene-functionalized fluorinated poly(arylene ether); and (c) heating the triazene-functionalized poly(arylene ether) to effect crosslinking.

In another embodiment, this invention provides a crosslinkable polymeric composition, comprising (a) fluorinated poly(arylene ether) repeat units of the structure

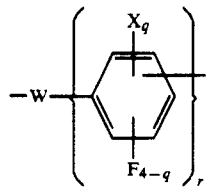

(X)

and (b) triazene-functionalized fluorinated poly(arylene ether) repeat units of the structure

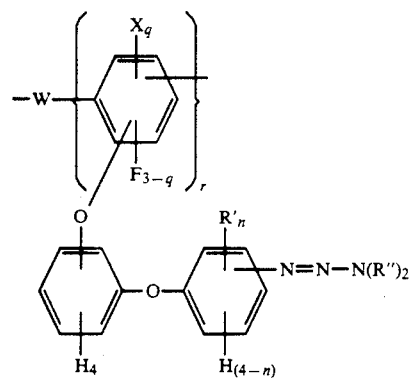

wherein
—W— is

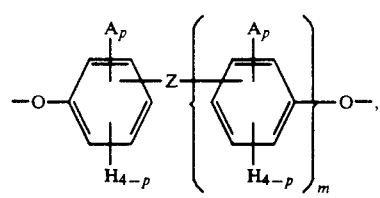

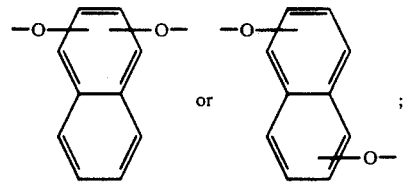

wherein each —A is independently —F, —Cl, —Br, —CF$_3$, —CH$_3$, —CH$_2$CH=CH$_2$, or —C$_6$H$_5$; p is 0, 1, or 2; —Z— is a direct bond, —C(CH$_3$)$_2$—, —C(CF$_3$)$_2$—, —O—, —S—, —SO$_2$—, —CO—, —P(C$_6$H$_5$)—, —C(CH$_3$)(C$_6$H$_5$)—, —C(C$_6$H$_5$)$_2$—, —(CF$_2$)$_{1-6}$—, or

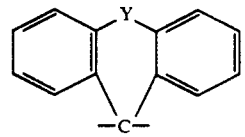

wherein —Y— is —O— or a direct bond; and m is 0, 1, or 2;
each —X is independently —H, —Cl, —Br, —CF$_3$, —CH$_3$, —CH$_2$CH=CH$_2$, or —C$_6$H$_5$;
q is 0, 1, or 2;
r is 1 or 2;
—R′ is —F, —CF$_3$, —CN, or —Cl; each —R′, which may be the same or different, is independently selected from the group consisting of C$_1$-C$_6$ alkyl or hydroxyalkyl moieties and aryl moieties; and n is 0 or 1.

DESCRIPTION OF THE PREFERRED EMBODIMENTS

For convenience of reference, in the 1-[(hydroxyphenoxy)phenylene]triazenes I

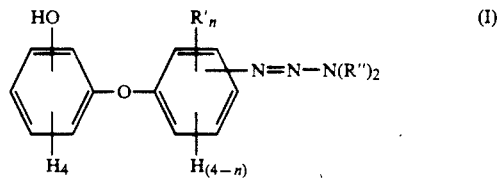

(I)

(where —R′, —R″, and n are as defined above) the ring positions of the HO— bearing ring are identified by the numerals 2 through 6, while the ring positions in the triazene bearing ring are identified by the numerals 2′ through 6′:

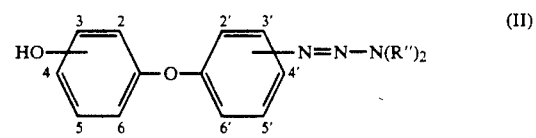

(II)

Preferred positions for the HO— group are 2 or 4. Preferred positions for the triazene moiety are 4′ or 2′. Preferably —R′ is —F or —CF$_3$. Preferably, —R′ is selected from the group consisting of —CH$_3$, —C$_6$H$_5$, and —CH$_2$CH$_2$OH. In one preferred embodiment, each —R″ is —CH$_3$. In an alternative preferred embodiment, at least one —R″ is —C$_6$H$_5$.

Specific preferred compounds I are shown below:

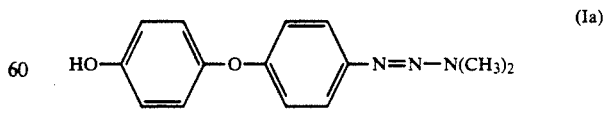

(Ia)

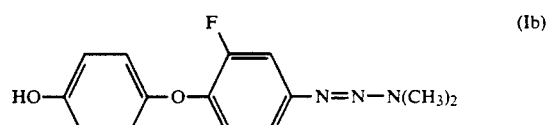

(Ib)

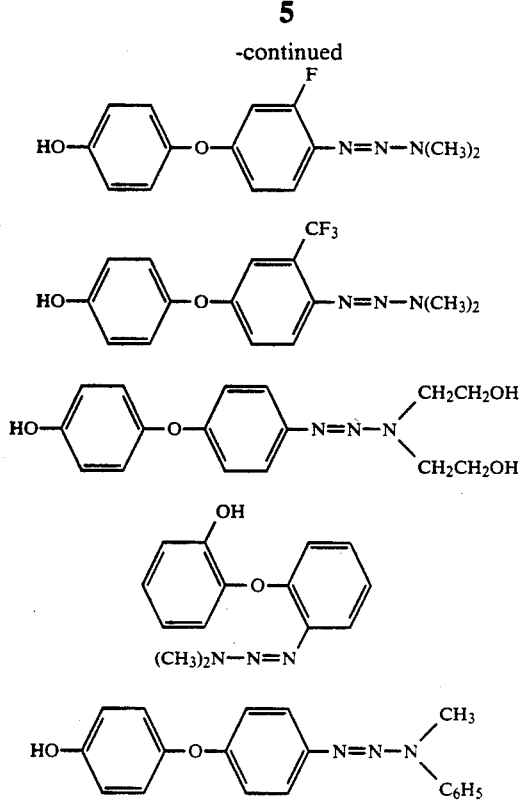

Compounds I can be prepared as follows (where —Q is —F, —Cl, or —Br):

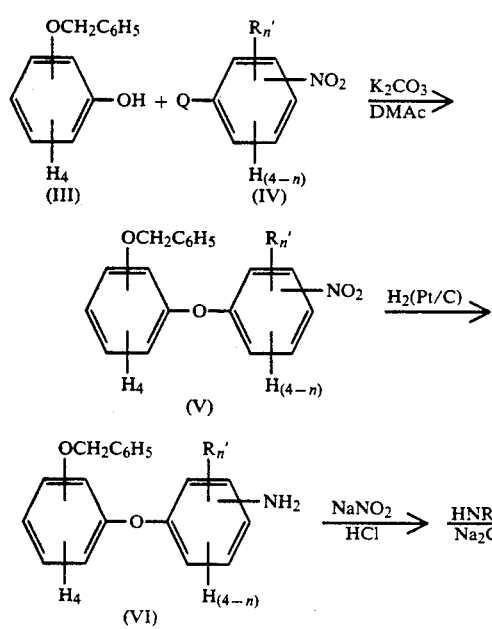

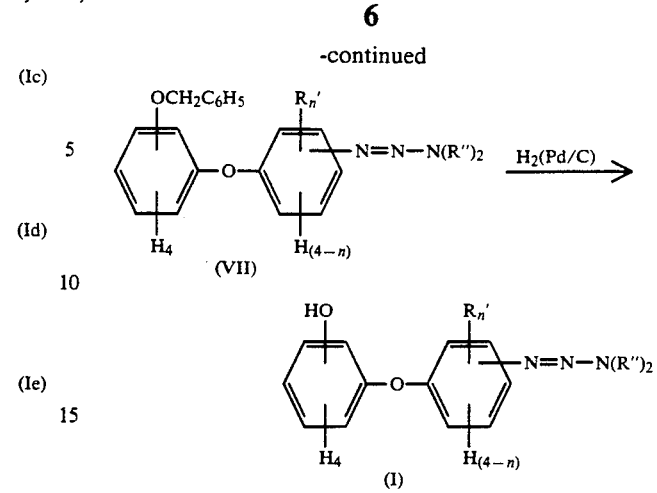

Structures of some specific precursor compounds V and VI are summarized in Table I:

TABLE I

| Compound V or VI | Compounds V and VI | | | —NO$_2$ or —NH$_2$ position |
|---|---|---|---|---|
| | C$_6$H$_5$CH$_2$O— position | n | R' | |
| Va, VIa | 4 | 0 | n/a | 4' |
| Vb, VIb | 4 | 1 | 2'-F | 4' |
| Vc, VIc | 4 | 1 | 3'-F | 4' |
| Vd, VId | 4 | 1 | 3'-CF$_3$ | 4' |
| Vf, VIf | 2 | 0 | n/a | 2' |

Structures of some specific precursor compounds VII are provided in Table II:

TABLE II

| Compound VII | Compounds VII | | | —N=N—N(R")$_2$ position | R" |
|---|---|---|---|---|---|
| | C$_6$H$_5$CH$_2$O- position | n | R' | | |
| VIIa | 4 | 0 | n/a | 4' | both CH$_3$ |
| VIIb | 4 | 1 | 2'-F | 4' | both CH$_3$ |
| VIIc | 4 | 1 | 3'-F | 4' | both CH$_3$ |
| VIId | 4 | 1 | 3'-CF$_3$ | 4' | both CH$_3$ |
| VIIf | 2 | 0 | n/a | 2' | both CH$_3$ |
| VIIg | 4 | 0 | n/a | 4' | one CH$_3$, one C$_6$H$_5$ |

An alternative synthetic approach to compounds I uses a diphenol such as hydroquinone (VIII) as a starting material, as illustrated below with particular reference to compound Ie:

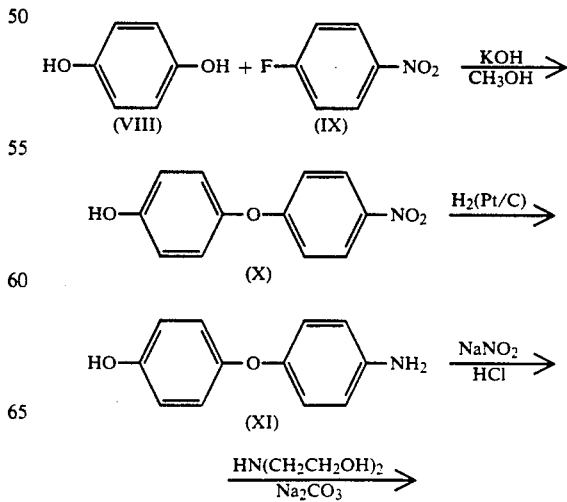

-continued

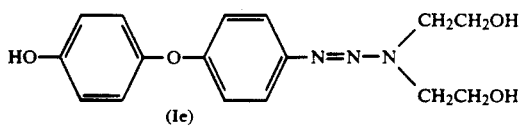

(Ie)

Fluorinated poly(arylene ethers) XII which can be crosslinked by compounds I

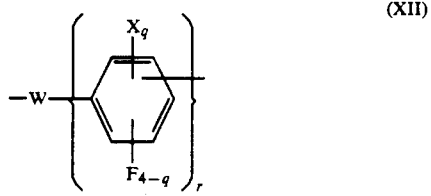

(XII)

can be prepared by the polymerization of a diphenol H—W—H with a fluorinated monomer XIII

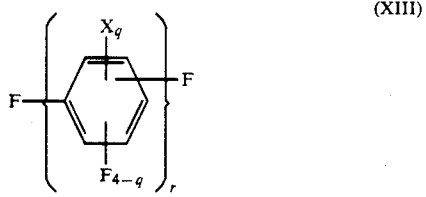

(XIII)

where —W—, —X, q, are as previously defined. Fluorinated poly(arylene ethers) XII preferably have a degree of polymerization between 6 and 100, more preferably between 6 and 50.

Suitable diphenols H—W—H include 4,4'-(hexafluoroisopropylidene)diphenol (also known as Bisphenol AF), 4,4'-isopropylidene-di(2,6-dimethylphenol), 4,4'-(1-phenylethylidene) bisphenol, 4,4'-isopropylidenediphenol (also known as Bisphenol A), 9,9'-bis(4-hydroxyphenyl)fluorene, 1,5-dihydroxynaphthalene, 2,7-dihydroxynaphthalene, resorcinol, and 4,6-dichlororesorcinol. Preferred ones include 4,4'-(hexafluoroisopropylidene)diphenol, 9,9'-bis(4-hydroxyphenyl)fluorene, and 1,5-dihydroxynaphthalene.

Suitable fluorinated monomers XIII include hexafluorobenzene, decafluorobiphenyl, pentafluorobenzene, octafluorotoluene, 1,4-dibromotetrafluorobenzene, chloropentafluorobenzene, allylpentafluorobenzene, and 2,2',3,3',5,5',6,6'-octafluorobiphenyl.

In the preparation of fluorinated poly(arylene ethers), a base such as an alkali metal carbonate, bicarbonate, or hydroxide is added to the polymerization mixture to convert the phenoxy groups to the corresponding phenoxides. Sodium and potassium carbonate are preferred. A polar aprotic solvent, such as N,N-dimethylacetamide (DMAc), N,N-dimethylformamide (DMF), or 1-methyl-2-pyrrolidinone (NMP) is used. The reaction is carried out at an elevated temperature, although such temperature should not be excessively high. A temperature between about 50° C. and about 125° C. is generally suitable, with a temperature between about 60° and about 90° C. being especially preferred. Reaction times are typically between about 10 and about 72 hours. The preparation of fluorinated poly(arylene ethers) XII is further described in allowed copending, commonly assigned application of Mercer et al., Ser. No. 07/583,897, filed Sep. 17, 1990, and in Mercer et al., U.S. Pat. Nos. 5,114,780 (1992) and 5,115,082 (1992), the disclosures of which are incorporated herein by reference.

We have discovered that, under alkaline conditions, the phenoxy group in compound I reacts with an aromatic fluorine in fluorinated poly(arylene ether) XII, displacing it and resulting in the attachment of compound I to produce a functionalized fluorinated poly(arylene ether) having some repeat units XII'. Typical conditions are 65° to 80° C. for 16 to 24 hr. Bases which can be used include sodium, potassium and cesium carbonates, pyridine, and triethylamine. The solvent can be DMAc, DMF, NMP, or some other polar aprotic solvent. The amount of compound I is typically between 0.1 and 10.0 mmol per g of fluorinated poly(arylene ether).

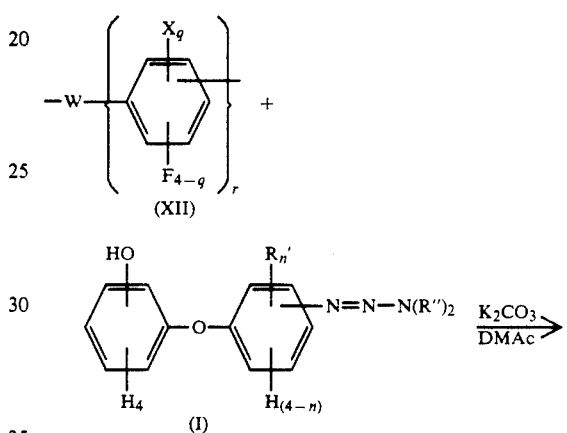

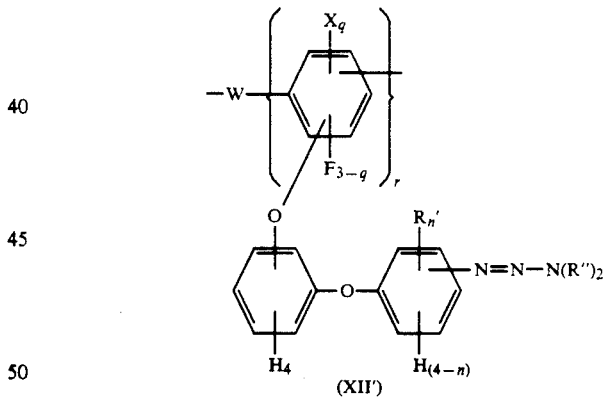

(XII')

The incorporation of compound I into fluorinated poly(arylene ether) XII to produce functionalized repeat units XII' was confirmed by $^1$H-NMR, IR, and $^{19}$F two dimension correlation spectroscopy (2D COSY). By varying the amount of compound I, the relative amounts of functionalized and unfunctionalized repeat units XII and XII' can be correspondingly varied. Functionalized but uncrosslinked fluorinated poly(arylene ether) exhibits little change in its molecular weight distribution, as indicated by gel permeation chromatography (GPC). As the amount of functionalized repeat units XII' increases, there is an increasing trend in the glass transition temperature of the crosslinked polymer.

It is believed that, when heated up to or above a threshold temperature, the triazene groups decompose to form phenyl radicals or other reactive centers. These then insert into aromatic groups in the fluorinated poly(arylene ether) to form aryl-aryl crosslinkages, as discussed in Lau et al., WO 91/09087 (1991), the disclosure of which is incorporated herein by reference. Generally, the functionalized fluorinated poly(arylene ether) is heated (soft baked) at a lower temperature, typically between 100° and 200° C., and then gradually heated to a higher final temperature, typically between 200° and 300° C. In one preferred set of crosslinking conditions, which was used with fluorinated poly(arylene ethers) functionalized with compounds I such as Ig, functionalized fluorinated poly(arylene ether) (coated on a plate) was first soft-baked in a convection oven at 100° C. for 60 min. It was then heated in a nitrogen oven (preheated to 100° C.) according to the following schedule: temperature increased from 100° to 215° C. at 5° C./min, temperature held constant 215° C. for 40 min, and temperature decreased from 215° to about 170° C. over 45 min. Finally, the material removed from the nitrogen oven and cooled to ambient temperature. In an alternative set of crosslinking conditions, which was used with fluorinated poly(arylene ethers) functionalized with compounds I such as Ia, Ib, Ic, and Id, the functionalized fluorinated poly(arylene ether) (coated on a plated) was first soft-baked in a convection oven at 100° C. for 30 min and then at 200° C. for another 30 min. It was then heated in a nitrogen oven (preheated to 200° C.) according to the following schedule: temperature increased from 200° to 300° C. at 3° C./min, temperature held constant at 300° C. for 30 min, and temperature decreased from 300° to 200° C. over 60 min. Finally, the material was removed from the nitrogen oven and cooled to ambient temperature. Those skilled in the art will appreciate that other suitable heating schedules may be found without undue experimentation.

Generally, after crosslinking, the fluorinated poly(arylene ether) XII has a very high gel content, greater than 90%. At levels of repeat unit XII' greater than 0.39 mmol per g of fluorinated poly(arylene ether), the resulting crosslinked polymer films do not exhibit solvent-induced stress crazing.

A method to lower the triazene decomposition (and therefore the crosslinking) temperature is to have at least one of the R" groups be an aromatic group, preferably phenyl. The aromatic group is believed to help stabilize radical centers on the adjacent nitrogen, leading to a lower decomposition temperature.

Fluorinated poly(arylene ethers) crosslinked according to this invention can be used in a variety of electronic applications, including as dielectrics in multichip modules or multilayer electronic interconnects, as protective layers or coatings in electronic article packaging, or as substrates for printed circuit boards.

Films or coatings of the uncrosslinked fluorinated poly(arylene ethers) can be formed by solution techniques such as spraying, spin coating, or casting, with spin coating being preferred. Preferred solvents are 2-ethoxyethyl ether, cyclohexanone, DMF, DMAc, methyl isobutyl ketone, 2-methoxyethyl ether, 5-methyl-2-hexanone, $\gamma$-butyrolactone, and mixtures thereof. Typically the coating thickness is between about 3 to about 15$\mu$.

Additives can be used to enhance or impart particular properties, as is conventionally known in the polymer art, including stabilizers, flame retardants, pigments, plasticizers, surfactants, and the like. Compatible or non-compatible polymers can be blended in to give a desired property.

The practice of this invention can be further understood by reference to the following examples, which are provided by means of illustration, not limitation. Those skilled in the art will also appreciate that polymers other than fluorinated poly(arylene ethers) can be functionalized and crosslinked with compounds I, applying the principles and methods disclosed herein.

The following general procedures and conditions apply to the examples. The reported melting points are uncorrected. The reported yields have not been optimized. Melting points were determined using a capillary melting point apparatus, unless noted otherwise. Dielectric constants of free standing polymer films were measured at 10 KHz by the method Mercer et al., "Developments of Low Moisture Absorbing, Low Dielectric Constant Dielectrics for Multichip Module Fabrication," *Proceed. Intern. Electron. Packaging Conf.*, Marlborough, Mass. (Sep. 1990), p. 1042. NMR spectra were recorded on a Varian XL-300 spectrometer, with chemical shifts expressed in ppm downfield from an internal tetramethylsilane standard for $^1$H spectra and in ppm upfield from an $\alpha,\alpha,\alpha$-trifluorotoluene internal standard for $^{19}$F spectra. IR spectra were recorded on a Perkin-Elmer 1420 spectrophotometer. Differential scanning calorimetry (DSC) and thermal gravimetric analysis (TGA) were performed with a Perkin-Elmer 7700 thermal analyzer at 10° C./min under a nitrogen atmosphere. Catalytic hydrogenation was performed with a Parr 3911 hydrogenation apparatus from Parr Instrument Co. Gel permeation chromatography (GPC) was performed with a Hewlett-Packard 1090 Liquid Chromatograph fitted with four Polymer Labs PL-Gel columns (100 Å, 500 Å, $10^3$ Å, and $10^4$ Å pore diameters) using tetrahydrofuran (THF) as eluent and polystyrene molecular weight standards.

EXAMPLE 1

A generally applicable procedure for the preparation of compounds V is illustrated by reference to compound Va: DMAc (40 mL), 4-benzyloxyphenol (14.0 g, 69.92 mmol), 1-fluoro-4-nitrobenzene (9.52 g, 67.47 mmol), and potassium carbonate (10.0 g, 72.35 mmol) were charged into a 500 mL flask equipped with a magnetic stirrer, a condenser, and a nitrogen inlet. The mixture was stirred at 120° C. for 16 hr and then poured into 0.2% sodium carbonate solution (500 mL). The mixture was stirred for 30 min and the precipitated product was filtered, washed with plenty of water, methanol (200 mL), and air dried. The crude product was recrystallized from boiling methanol (900 mL) to give compound Va (17.44 g, 85% yield).

Yield, melting point (mp) and $^1$H-NMR results for various analogously prepared compounds V are provided in Table III. Additionally, IR spectra were obtained and were consistent with the assigned structures.

TABLE III

| | Characteristics of Precursor Compounds V | | |
|---|---|---|---|
| Compound | Yield (%) | mp (°C.) | $^1$H-NMR (ppm) |
| Va | 85 | 110–112 | 5.11(s, 2H), 7.05(d, 2H), 7.12(s, 5H), 7.30– |

TABLE III-continued

Characteristics of Precursor Compounds V

| Compound | Yield (%) | mp (°C.) | ¹H-NMR (ppm) |
|---|---|---|---|
| Vb | 98 | 120–123 | 7.50(m, 4H), 8.22(d, 2H)[a] 5.14(s, 2H), 7.0–7.21(m, 5H), 7.30–7.53(m, 5H), 8.04(dd, 1H), 8.15(dd, 1H)[b] |
| Vc | 20 | 99–101 | 5.11(s, 2H), 6.79(dd, 1H), 7.08–7.19(m, 4H), 7.33–7.49(m, 6H), 8.18(dd, 1H)[a] |
| Vd | 62 | 93–5 | 5.12(s, 2H), 7.10–7.48(m, 11H), 8.18(d, 1H)[a] |
| Vf | 97 | (Oil) | 5.07(s, 2H), 6.83(d, 1H), 7.0–7.4(m, 10H), 7.57(t, 1H), 7.98(d, 1H)[a] |

[a]Dimethylsulfoxide-$d_6$ solvent
[b]Acetone-$d_6$ solvent

EXAMPLE 2

A generally applicable procedure for the preparation of compounds VI is illustrated by reference to compound VIa: Compound Va (8.0 g), 0.5% platinum catalyst on activated charcoal (1.6 g), and THF (100 mL) were charged into a 250 mL hydrogenation vessel. The hydrogenation was carried out at 60 psi hydrogen for 3 hr. The reaction mixture was filtered and the solvent was removed under reduced pressure at 50° C. The residue was recrystallized from THF/hexanes to give compound VIa (7.0 g, 97% yield).

Yield, melting point (mp) and ¹H-NMR results for various analogously prepared compounds VI are provided in Table IV. Additionally, IR spectra were obtained and were consistent with the assigned structures.

TABLE IV

Compounds VI

| Compound | Yield (%) | mp (°C.) | ¹H-NMR (ppm) |
|---|---|---|---|
| VIa | 97 | 132–5 | 3.57(s, 2H), 5.13(s, 2H), 6.40–7.0(m, 7H), 7.20–7.50(m, 6H)[a] |
| VIb | 76 | 124–7 | 5.07(s, 2H), 6.90–7.15(m, 6H), 7.25–7.50(m, 6H)[b] |
| VIc | 98 | 39–42 | 4.62(s, 2H), 4.90(s, 2H), 6.12–6.70(m, 3H), 6.75–6.90(m, 4H), 7.02–7.42(m, 5H)[c] |
| VId | 62 | 93–5 | 5.12(s, 2H), 7.10–7.48(m, 11H), 8.18(d, 1H)[c] |
| VIf | 98 | (Oil) | 4.89(s, 2H), 5.14(s, 2H), 6.45–7.50(m, 13H)[c] |

[a]CDCl₃ solvent
[b]HCl salt in dimethylsulfoxide-$d_6$ solvent
[c]Dimethylsulfoxide-$d_6$ solvent

EXAMPLE 3

A generally applicable procedure for the preparation of compounds VII is illustrated by reference to compound VIIa: A solution of 12N hydrochloric acid (12.2 mL, 145.9 mmol) in water (100 mL) was slowly added with stirring to a solution of compound VIa (8.0 g, 36.5 mmol) in THF (150 mL). The resulting solution was chilled to −5° C. with vigorous stirring. A solution of sodium nitride (3.77 g, 54.71 mmol) in water (50 mL) was added dropwise over a period of 30 min to the chilled solution. Stirring was continued for an additional 60 min at about −2° C. At the end of the reaction time, dimethylamine hydrochloride (5.95 g, 72.94 mmol) in water (30 mL) was added to the reaction mixture, followed immediately by sodium carbonate (19.33 g, 182.36 mmol) in water (50 mL). After stirring for 10 min at about 0° C., the THF was removed under reduced pressure at 25° C. The reaction mixture was extracted with dichloromethane (4×50 mL). The combined extracts were washed twice with distilled water, dried over anhydrous magnesium sulfate, and decolorized with activated charcoal. The dichloromethane was removed under reduced pressure at 35° C. and the residue chromatographed through a 2.5 inch internal diameter column packed with aluminum oxide (250 g), using THF/hexane (1:3 v:v) as the mobile phase to give compound VIIa (8.29 g, 76% yield).

Yield, melting point (mp), decomposition temperature ($T_d$), and ¹H-NMR results for various analogously prepared compounds VII are provided in Table V. Additionally, IR spectra were obtained and were consistent with the assigned structures.

TABLE V

Compounds VII

| Compound | Yield (%) | mp (°C.) | $T_d$ (°C.)[a] | ¹H-NMR (CDCl₃, ppm) |
|---|---|---|---|---|
| VIIa | 76 | 84–6 | 284 | 3.25(s, 6H), 5.05(s, 2H), 6.80–7.10(m, 6H), 7.22–7.45(m, 7H) |
| VIIb | 67 | 71[a] | 288 | 3.30(d, 6H), 5.05(s, 2H), 6.72–7.60(m, 12H) |
| VIIc | 28 | 76[a] | 222 | 3.22(s, 6H), 5.50(s, 2H), 6.72–7.50(m, 12H) |
| VIId | 10 | (Oil) | 303 | 3.33(d, 6H), 5.05(s, 2H), 6.95–7.55(m, 12H) |
| VIIf | 79 | (Oil) | 271 | 3.90(s, 3H), 3.35(s, 3H), 5.12(s, 2H), 6.75–7.40(m, 13H) |
| VIIg | 89 | 110–113 | 200 | 3.66(s, 6H), 5.08(s, 2H), 7.00–7.60(m, 18H) |

[a]By DSC at 10° C./min under nitrogen ($T_d$ = exothermic decomposition peak temperature)

EXAMPLE 4

A generally applicable procedure for the preparation of compounds I from compounds VII is illustrated by reference to compound Ia.

To a solution of compound VIIa (7.00 g) in THF (20 mL), 1% palladium catalyst on activated charcoal (1.0 g) was added, followed by ethanol (100 mL). The hydrogenation was carried out at room temperature under 60 psi pressure for 16 hr. The reaction mixture was filtered and the organic solvent was removed under reduced pressure at 40° C. to give compound Ia (5.03 g, 97% yield).

EXAMPLE 5

This example illustrates the alternative synthetic route to compounds I, with hydroquinone as a starting material and compound Ie as the final product: Hydroquinone (8.00 g, 72.65 mmol), 1-fluoro-4-nitrobenzene (10.00 g, 70.87 mmol), potassium hydroxide (4.08 g, 72.65 mmol), and methanol (250 mL) were charged into a 500 mL flask equipped with a magnetic stirrer, condenser, and nitrogen inlet. The reaction mixture was gently refluxed with good stirring under nitrogen atmosphere for 24 hr. The reaction mixture was then cooled to room temperature and filtered. Methanol from the filtrate was removed under reduced pressure at 40° C. The residue was washed with water until the washings were colorless. The resulting solid was then redissolved in 2% aqueous potassium hydroxide (200) and filtered. The dark red aqueous solution was then acidified with 12N hydrochloric acid. The precipitated product was filtered, washed with plenty of water, suction dried, and vacuum dried at 50° C. overnight to give 1-(4-hydroxyphenoxy)-4-nitrobenzene X (9.30 g, 56.8%) as a light yellow powder, mp 170°–3° C. The IR and $^1$H-NMR spectra agreed with the assigned structure.

1-(4-Hydroxyphenoxy)-4-nitrobenzene X (8.93 g, 38.62 mmol), 0.5% platinum catalyst on activated charcoal (1.5 g), THF (100 mL), and ethyl acetate (20 mL) were charged into a 250 mL hydrogenation vessel. Hydrogenation was carried out under 60 psi of hydrogen at room temperature for 16 hr. The reaction mixture was filtered and the organic solvents were removed under reduced pressure at 40° C. to give 4-(4-aminophenoxy)phenol XI (8.10 g, 96.2% yield), mp 130°–4° C. The IR and $^1$H-NMR spectra agreed with the assigned structure.

4-(4-Aminophenoxy)phenol XI (3.50 g, 17.39 mmol), water (100 mL), and 10N hydrochloric acid (6.0 mL, 60 mmol) were charged into a 500 mL flask equipped with an addition funnel, thermometer, and mechanical stirrer. The resulting solution was chilled to −2° C. in a salt-ice bath with vigorous stirring. Sodium nitrite (1.44 g, 20.87 mmol) in water (50 mL) was added dropwise to the chilled solution, taking care to maintain the temperature of the solution at 0° C. during the addition. After the addition was complete, the solution was stirred for 2 hr at 0° C. under a nitrogen atmosphere. The reaction mixture was suction-filtered and the bright yellow filtrate was collected in a flask containing crushed ice. A solution in water (50 mL) of diethanolamine (3.66 g, 34.79 mmol) was added to the filtrate with stirring, followed immediately by the addition of a solution of sodium carbonate (5.53 g, 52.18 mmol) in water (50 mL). The reaction mixture was then stirred at ambient temperature for 20 min. The upper aqueous layer was discarded after standing for 10 min. The residual oil was redissolved in 100 mL of methanol and dried over anhydrous magnesium sulfate. After the removal of methanol under reduced pressure at 40° C., the oily residue was chromatographed through a 2.5 inch internal diameter column packed with aluminum oxide (200 g) with methanol as the mobile phase to yield compound Ie (1.52 g, 28% yield) as an orange oil.

Yield, melting point (mp) and $^1$H-NMR results for various compounds I prepared by the method of Example 4 or Example 5 are provided in Table VI. Additionally, IR spectra were obtained and were consistent with the assigned structures.

TABLE VI

| Compound | Yield (%) | mp (°C.) | $^1$H-NMR (CDCl$_3$, ppm) |
|---|---|---|---|
| Ia | 92 | 120–3 | 3.30(s, 6H), 6.77(d, 2H), 6.86–6.94(m, 4H), 7.36(d, 2H), 8.30(s, 1H) |
| Ib | 90 | 132[a] | 3.13(s, 3H), 3.44(s, 3H), 6.75(d, 2H), 6.84 (d, 2H), 6.94(t, 1H), 7.10(m, 1H), 7.24(m, 1H), 9.30(s, 1H) |
| Ic | 77 | —[b] | 3.05(s, 3H), 3.40(s, 3H), 6.68(t, 1H), 6.70 (d, 2H), 6.79(d, 2H), 7.10(m, 1H), 7.34 (m, 1H), 9.28(s, 1H) |
| Id | 86 | —[b] | 3.05(s, 3H), 3.40(s, 3H), 7.05(t, 1H), 6.80 (d, 2H), 6.91(d, 2H), 7.23(m, 1H), 7.50(m, 1H), 9.28(s, 1H) |
| Ie | 28 | —[b] | 3.80–3.94(m, 8H), 4.35(b, 2H), 6.75–6.95 (m, 6H), 7.34(d, 2H) |
| If | 99 | —[b] | 3.05(s, 3H), 3.46(s, 3H), 6.65–7.40(m, 8H), 9.37(s, 1H) |
| Ig | 79 | 81–3 | 3.62(s, 3H), 6.85–7.51(m, 13H)[c] |

[a]By DSC at 10° C./min under nitrogen (exothermic decomposition peak maximum)
[b]Liquid at ambient temperature
[c]Acetone-d$_6$

EXAMPLE 6

This example provides a generally applicable procedure for the functionalization of fluorinated poly(arylene ethers) with compounds I, illustrated by particular reference to a fluorinated poly(arylene ether) having repeat units XIIa

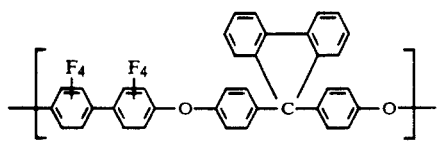

(XIIa)

and to compound Ia.

Fluorinated poly(arylene ether) XIIa (3.00 g), compound Ia (0.30 g, 1.17 mmol), potassium carbonate powder (0.30 g 23.40 mmol), and DMAc (25 mL) were charged into a 50 mL flask equipped with a magnetic stirrer and nitrogen inlet. The reaction mixture was stirred at 80° C. under nitrogen for 16 hr. The reaction mixture was then poured into a methanol-water mixture (400 mL, 1:3 v:v) with vigorous stirring. The precipitate was filtered, washed with plenty of water and then methanol (150 mL), suction air dried, and vacuum dried at 40° C. overnight, to give a functionalized polymer (2.87 g, 88% yield) comprising repeat units XIIa and modified repeat units XIIa′ (R′=H, each R″=CH₃).

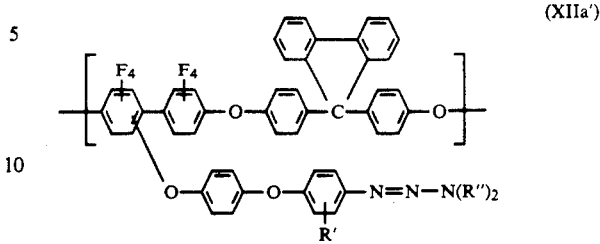

(XIIa′)

The results for a series of experiments with different amounts of compound Ia are provided in Table VII. Additionally, IR spectra were obtained, which were consistent with the assigned structures.

TABLE VII

| | Crosslinking of Fluorinated Poly(arylene ether) XIIa with Compound Ia | | | |
|---|---|---|---|---|
| | Compound Ia added (mmol per g XIIa) | | | |
| | 0.0 (control) | 0.19 | 0.39 | 0.65 |
| Before curing | | | | |
| XIIa/XIIa′ ratio[a] | n/a | 7 | 3.6 | 1.5 |
| GPC $M_n$ | 15,000 | 18,300 | 19,200 | 20,100 |
| $M_w$ | 54,400 | 68,900 | 69,800 | 82,670 |
| ¹H-NMR (CDCl₃, ppm) | — 6.75–6.98 (m), 7.10–7.60 (m), 7.70–7.90 (m) | 3.32 (s), 6.60–7.00 (m), 7.00–7.60 (m), 7.70–7.90 (m) | 3.32(s), 6.60–7.20(m), 7.20–7.50(m), 7.63–7.90(m) | 3.32 (s), 6.60–7.00 (m), 7.00–7.50 (m), 7.60–7.85 (m) |
| ¹⁹F-NMR (CDCl₃, ppm) | −139.05 (m) — — — −153.76 (m) — | −139.05 (m) −139.26 (m) −144.72 (m) −152.92 (m) −153.76 (m) −154.35 (m) | −139.05(m) −139.26(m) −144.72(m) −152.92(m) −153.76(m) −154.35(m) | −139.05 (m) −139.26 (m) −144.72 (m) −152.92 (m) −153.76 (m) −154.35 (m) |
| $T_d$ (°C.)[b] | n/a | 291 | 293 | 290 |
| Cured (300° C.) | | | | |
| $T_g$ (°C.)[b] | 258 | 278 | 279 | 297 |
| ε[c] 0% RH | 2.69 | 2.70 | 2.75 | — |
| 60% RH | 2.84 | 2.80 | 2.88 | — |
| Gel content (%) | ~1 | 99.8 | 99.9 | 99.9 |
| Stress crazing | Yes | Yes | No | No |

[a]Measured by ¹H-NMR integration
[b]Measured by DSC at 10° C./min under nitrogen
[c]Dielectric constant measured at 10 KHz Following the above procedure, fluorinated poly(arylene ether) XIIa was also functionalized with compounds Ib, Ic, and Id. The results are provided in Table VIII. IR spectra were also obtained and were consistent with the assigned structures.

TABLE VIII

| | Crosslinking of Fluorinated Poly(arylene ether) XIIa with Compounds I | | | |
|---|---|---|---|---|
| | Compound I added (0.39 mmol per g XIIa) | | | |
| | Ia (R′ = H) | Ib (R′ = 2′-F) | Ic (R′ = 3′-F) | Id (R′ = 3′-CF₃) |
| Before curing | | | | |
| XIIa/XIIa′ ratio[a] | 3.6 | 3.8 | 3.6 | 3.9 |
| GPC $M_n$ | 19,200 | 17,000 | 16,100 | 21,000 |
| $M_w$ | 69,800 | 119,400 | 87,000 | 118,100 |
| ¹H-NMR (CDCl₃, ppm) | 3.32 (s) 6.60–7.20 (m), 7.20–7.50 (m), 7.63–7.90 (m) | 3.32 (s), 6.65–7.05 (m), 7.10–7.44 (m), 7.70–7.84 (m) | 3.32 (s), 6.60–7.00 (m), 7.10–7.55 (m), 7.65–7.86 (m) | 3.32 (s), 6.60–7.00 (m), 7.10–7.60 (m), 7.70–7.90 (m) |
| ¹⁹F-NMR (CDCl₃, ppm) | — −139.05 (m) −139.26 (m) −144.72 (m) −152.92 (m) −153.76 (m) −154.35 (m) | −116.66 (t) −139.05 (m) −139.26 (m) −144.72 (m) −152.92 (m) −153.76 (m) −154.35 (m) | −130.78 (t) −139.05 (m) −139.26 (m) −144.72 (m) −152.92 (m) −153.76 (m) −154.35 (m) | −61.16 (s) −139.05 (m) −139.26 (m) −144.72 (m) −152.92 (m) −153.76 (m) −154.35 (m) |
| $T_d$ (°C.)[b] | 293 | 291 | 293 | 290 |

TABLE VIII-continued

Crosslinking of Fluorinated Poly(arylene ether) XIIa with Compounds I

| | Compound I added (0.39 mmol per g XIIa) | | | |
|---|---|---|---|---|
| | Ia (R' = H) | Ib (R' = 2'-F) | Ic (R' = 3'-F) | Id (R' = 3'-CF$_3$) |
| After curing (300° C.) | | | | |
| T$_g$ (°C.)[b] | 279 | 297 | 300 | 309 |
| TGA[b] | | | | |
| Onset wt loss (°C.) | 550 | 556 | 551 | 552 |
| °C. @5% wt loss | 533 | 542 | 496 | 533 |
| % wt loss @700° C. | 77.3 | 98.6 | 99.3 | 99.5 |
| Isothermal wt loss in air (3 hr/400° C.) (%) | 8.3 | 4.0 | 5.0 | 4.6 |
| Gel content (%) | 99.9 | 99.4 | 99.4 | 94.3 |
| Stress crazing | No | Yes | Yes | Yes |

[a]Measured by $^1$H-NMR integration
[b]Measured by DSC or TGA at 10° C./min under nitrogen

EXAMPLE 7

Following the general procedure of Example 6, fluorinated poly(arylene ether) XIIb was functionalized by reaction with compound Ia to give repeat units XIIb' (each —R" equals —CH$_3$).

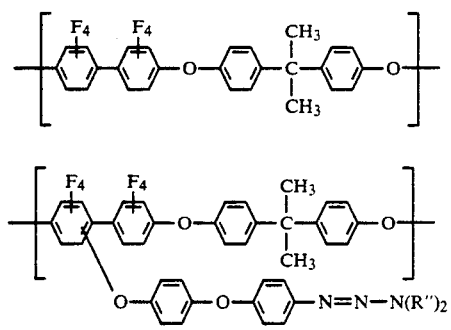

The results are provided in Table IX. Additionally, IR spectra were obtained, which were consistent with the assigned structures.

TABLE IX

Crosslinking of Fluorinated Poly(arylene ether) XIIb with Compound Ia

| | Compound Ia added (mmol per g XIIb) | |
|---|---|---|
| | 0.0 (control) | 0.58 |
| Before curing | | |
| XIIb/XIIb' ratio[a] | n/a | 3.8 |
| GPC M$_n$ | 22,800 | 30,620 |
| M$_w$ | 345,600 | 788,200 |
| $^1$H-NMR (CDCl$_3$, ppm) | — | 3.29 (s) |
| | 7.06 (d) | 6.70-7.15 (m) |
| | 7.40 (d) | 7.21-7.50 (m) |
| T$_d$ (°C.)[b] | n/a | 283 |
| Cured (300° C.) | | |
| T$_g$ (°C.)[b] | 189 | 236 |
| ε[c] 0% RH | 2.46 | 2.56 |
| 60% RH | 2.56 | 2.83 |
| Gel content (%) | 0 | 99.7 |
| Stress crazing | Yes | No |

[a]Measured by $^1$H-NMR integration
[b]Measured by DSC at 10° C./min under nitrogen
[c]Dielectric constant measured at 10 KHz

EXAMPLE 8

Following the general procedure of Example 6, fluorinated poly(arylene ether) XIIa was functionalized with repeat units XIIa' (—R'=—H, one —R"=—CH$_3$, one —R"=—C$_6$H$_5$) by reaction with compound Ig.

The results are provided in Table X. Additionally, IR spectra were obtained, which were consistent with the assigned structures.

TABLE X

Crosslinking of Fluorinated Poly(arylene ether) XIIa with Compound Ig

| | Compound Ig added (mmol per g XIIa) | | |
|---|---|---|---|
| | 0.0 (control) | 0.39 | 0.63 |
| Before curing | | | |
| XIIa/XIIa' ratio[a] | n/a | 4.0 | 2.5 |
| GPC M$_n$ | 15,000 | 25,190 | 18,300 |
| M$_w$ | 54,400 | 1,041,000 | 691,400 |
| $^1$H-NMR (CDCl$_3$, ppm) | — | 3.63 (s) | 3.63 (s) |
| | 6.80-698 (m) | 6.70-7.00 (m) | 6.70-7.0 (m) |
| | 7.10-7.47 (m) | 7.00-7.55 (m) | 7.10-7.55 (m) |
| | 7.68-7.84 (m) | 7.65-7.85 (m) | 7.70-7.85 (m) |
| T$_d$ (°C.)[b] | n/a | 212 | 209 |
| Cured (300° C.) | | | |
| T$_g$ (°C.)[b] | 258 | 274 | 288 |
| ε[c] 0% RH | 2.71 | 2.72 | 2.73 |
| 60% RH | 2.82 | 2.97 | 2.95 |
| Gel content (%) | 0 | 92 | 97 |
| Stress crazing | Yes | No | No |

[a]Measured by $^1$H-NMR integration
[b]Measured by DSC at 10° C./min under nitrogen
[c]Dielectric constant measured at 10 KHz

EXAMPLE 9

Fluorinated poly(arylene ether) XIIb was functionalized with repeat units XIIb' (one —R" equals —CH$_3$, one —R" equals —C$_6$H$_5$) by reaction with compound Ig.

Fluorinated poly(arylene ether) XIIb (0.30 g, 1.17 mmol), potassium carbonate powder (0.30 g, 23.40 mmol), and DMAc (30 mL) were charged into a 50 mL flask equipped with a magnetic stirrer and nitrogen inlet. The reaction mixture was stirred at 75° C. under nitrogen for 20 hr. The reaction mixture was poured into methanol/water mixture (400 mL, 1:3 v/v) with vigorous stirring. The precipitated polymer was filtered, washed with plenty of water and then methanol (150 mL), suction air dried, and vacuum dried at 40° C. overnight to give product (2.56 g, 77% yield).

The results are provided in Table XI. Additionally, IR spectra were obtained, which were consistent with the assigned structures.

TABLE XI

Crosslinking of Fluorinated Poly(arylene ether) XIIb with Compound Ig

| | Compound Ig added (mmol per g XIIb) | |
|---|---|---|
| | 0.0 (control) | 0.39 |
| Before curing | | |
| XIIb/XIIb' ratio[a] | n/a | 3.92 |
| GPC $M_n$ | 22,800 | 32,000 |
| $M_w$ | 345,600 | 1,481,000 |
| $^1$H-NMR (CDCl$_3$, ppm) | — | 3.61 (s) |
| | 7.06 (d) | 6.70–7.18 (m) |
| | 7.40 (d) | 7.75–7.60 (m) |
| $T_d$ (°C)[b] | n/a | 208 |
| Cured (300° C.) | | |
| $T_g$ (°C)[b] | 189 | 218 |
| $\epsilon^c$ 0% RH | 2.46 | 2.65 |
| 60% RH | 2.56 | 2.76 |
| Gel content (%) | 0 | 98 |
| Stress crazing | Yes | No |

[a]Measured by $^1$H-NMR integration
[b]Measured by DSC at 10° C./min under nitrogen
[c]Dielectric constant measured at 10 KHz

What is claimed is:

1. A compound of the structure

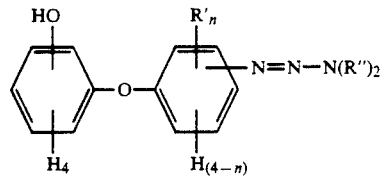

where —R' is —F, —CF$_3$, —CN, or —Cl; each —R", which may be the same or different, is independently selected from the group consisting of C$_1$-C$_6$ alkyl or hydroxyalkyl moieties and aryl moieties; and n is 0 or 1.

2. A compound according to claim 1, wherein the HO— group in the 4-position.

3. A compound according to claim 1, wherein n is 0.

4. A compound according to claim 1, wherein n is 1 and —R' is —F or —CF$_3$.

5. A compound according to claim 1, wherein at least one —R" is phenyl.

6. A compound according to claim 1, wherein each —R" is —CH$_3$.

7. A compound according to claim 1, selected from the group consisting of

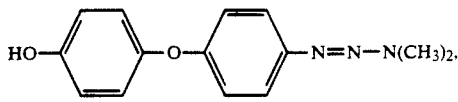

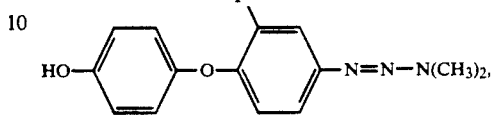

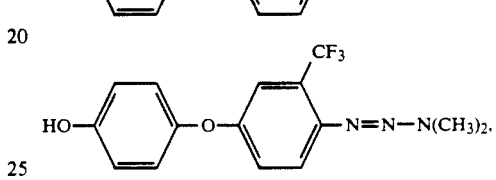

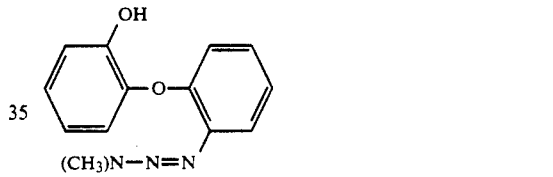

and

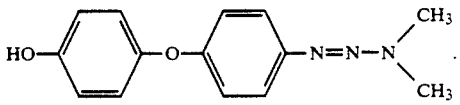

* * * * *